(12) United States Patent
Mohapatra et al.

(10) Patent No.: US 8,536,324 B2
(45) Date of Patent: Sep. 17, 2013

(54) METHOD OF DRUG DELIVERY BY CARBON NANOTUBE-CHITOSAN NANOCOMPLEXES

(75) Inventors: Shyam S. Mohapatra, Tampa, FL (US); Arun Kumar, Tampa, FL (US)

(73) Assignee: University of South Florida, Tampa, FL (US)

( * ) Notice: Subject to any disclaimer, the term of this patent is extended or adjusted under 35 U.S.C. 154(b) by 805 days.

(21) Appl. No.: 12/105,884

(22) Filed: Apr. 18, 2008

(65) Prior Publication Data

US 2008/0214494 A1 Sep. 4, 2008

Related U.S. Application Data

(63) Continuation of application No. PCT/US2006/041570, filed on Oct. 23, 2006.

(60) Provisional application No. 60/729,461, filed on Oct. 21, 2005.

(51) Int. Cl.
*C08B 37/08* (2006.01)
*C01B 31/00* (2006.01)

(52) U.S. Cl.
CPC ............ *C08B 37/003* (2013.01); *Y10S 977/742* (2013.01); *Y10S 977/75* (2013.01); *Y10S 977/753* (2013.01)
USPC ........... 536/55.1; 977/742; 977/750; 977/753

(58) Field of Classification Search
None
See application file for complete search history.

(56) References Cited

U.S. PATENT DOCUMENTS

| | | | |
|---|---|---|---|
| 5,744,166 A | 4/1998 | Illum | |
| 6,184,037 B1 | 2/2001 | Rolland et al. | |
| 6,391,318 B1 | 5/2002 | Illum et al. | |
| 7,118,881 B2 * | 10/2006 | Lee et al. | 435/14 |
| 2004/0076681 A1 | 4/2004 | Dennis et al. | |
| 2005/0037374 A1 | 2/2005 | Melker et al. | |
| 2006/0134220 A1 | 6/2006 | Aboubakar et al. | |

FOREIGN PATENT DOCUMENTS

| | | | |
|---|---|---|---|
| WO | 02076888 A1 | 10/2002 | |
| WO | WO2005/121799 | * 12/2005 | |

OTHER PUBLICATIONS

Zhang et al., "Carbon Nanotube-Chitosan System for Electrochemical Sensing Based on Dehydrogenase Enzymes" Analytical Chemistry (2004) vol. 76 pp. 5045-5050.*
Jiang et al., "Electrochemical oxidation behavior of nitrite on a chitosan-carboxylated multiwall carbon nanotube modified electrode" Electrochemistry Communications (2005) vol. 7 pp. 597-601.*
Trademark Registration for Nanogene®, downloaded from tess2.uspto.gov, filed Apr. 28, 2004.*
Chemical Abstracts Regidtry entry for Nanogene 042, entered Chem Abstracts Registry Jul. 13, 2005.*
Tan et al., "An amperometric cholesterol biosensor based on multiwalled carbon nanotubes and organically modified sol-gel/chitosan hybrid composite film" Analytical Biochemistry (2005) vol. 337, pp. 111-120.*
Nunez et al. 2010. "Hybrid Polymer-Grafted Multiwalled Carbon Nanotubes fir In Vitro Gene Delivery." Small. vol. 6. No. 20. pp. 2281-2291.

* cited by examiner

*Primary Examiner* — Eric S Olson
(74) *Attorney, Agent, or Firm* — Robert J. Varkonyi; Smith & Hopen, P.A.

(57) ABSTRACT

Functionalized Single Wall Carbon Nanotube (SWCNT) complexed with nanochitosan for use in the delivery of bio-affecting substances and diagnostic applications. fSWCNT complexed with the chitosan NG042 were used for delivery of DNA-encoding EGFP reporter protein and peptide. The results demonstrate that shown CNT-chitosan hybrid nanoparticles exhibit significantly higher transfection efficiency in vivo than chitosan alone. Furthermore, the functionalized nanotubes were tested for peptide transfer into HEK293 cells. The results showed that the hybrid nanoparticles efficiently transferred peptides. Together, these results show that hybrid SWCNT-chitosan particles increase DNA and peptide transfer into cells.

18 Claims, 3 Drawing Sheets

METHOD OF DRUG DELIVERY BY CARBON NANOTUBE-CHITOSAN NANOCOMPLEXES

CROSS REFERENCE TO RELATED APPLICATIONS

This application is a continuation of prior filed International Application, Serial Number PCT/US2006/041570 filed Oct. 23, 2006, which claims priority to U.S. provisional patent application No. 60/729,461 filed Oct. 21, 2005 which is hereby incorporated by reference into this disclosure.

FIELD OF INVENTION

This invention relates to drug delivery systems. More specifically, this invention relates to methods of preparing carbon nanotube-chitosan complexes nanocomplexes and their use in diagnostic and drug delivery systems.

BACKGROUND OF THE INVENTION

The combination of nanoscale structures with biomolecules opens the door to novel biology and nanotechnology applications [1-6]. Controls over the material structure at the nanoscale are revolutionizing a wide range of fields and applications. This leads to improved characteristics and functions, as well as significant enhancement of optical, mechanical, electrical, structural, and magnetic properties of nanomaterials. Nanoparticles have been employed for a number of applications such as enzyme immobilization and drug delivery systems to solve various health problems. Nanomaterials are expected to have further impact on biomedicine, biosensors, diagnostics, and drug delivery systems [7-9].

Carbon nanotubes (CNTs) and their compatibility with aqueous environments have made it possible to interact with biological components including mammalian cells. Chemical functionalization of CNT surface, allows the functionalized CNT molecules (f-CNT) to be explored in advanced biotechnological applications. Functionalization is one of the most commonly used strategies to make CNT soluble in aqueous media. It makes f-CNT useful for biomedical applications. Carbon nanotubes can be functionalized either by covalent or noncovalent methodologies. Various biological applications of functionalized carbon nanotubes (f-CNTs) include their use as substrates for neuronal cell growth, as bioseparators and biocatalysts [10-14].

Recently, carbon nanotube-based field-effective-transistors (FET) have been developed which are used for DNA-based biomolecular recognition. Carbon nanotubes attached with single-strand DNA chains (ssDNAs) are used as probes for detecting their complementary DNA molecules specifically grafted over the FET substrate. The hybridization is detected by using redox method [15-18]. Carbon nanotubes can be used as stores for DNA or peptide molecules which have high potential in gene delivery system and molecular therapy of diseases [19-20].

Carbon nanotubes can also be used to fabricate nanomotors, which can enter inside the cells to treat diseases. So far, the influence of carbon nanotubes and the associated nanomaterials or nanodevices on human health and environment has been a focus of current investigation. Carbon nanotubes can be functionalized to achieve improved properties and functions such as biocompatibility and biomolecular recognition capabilities [21-22]. The potential with which carbon nanotubes can be applied in biomedical engineering and medicinal chemistry is highly dependent upon their biocompatibility. Carbon nanotubes exhibit cytotoxicity to human keratinocyte cells [23-24], can inhibit the growth of embryonic rat-brain neuron cells [25] and induce the formation of mouse-lung granulomas [26-28]. Computational model has shown that CNT fits snugly into the major groove of double standard DNA, since the diameter of single-walled CNT is compatible with the size of the DNA major groove. Moreover, CNT is a semi conducting material which offers the possibility of being used as switching device. The geometry of the combined DNA and CNT system was modeled using the CHARMM computational package with a properly adapted graphitic carbon force field for treating CNTs. Hybridization of electronic orbital between the CNT and the DNA is also included in this model [29-31]. In another approach, streptavidin-functionalized SWCNT was directed to the right location on the scaffold dsDNA molecule. SWNTs were solubilized in water by micellization in SDS. The solubilized SWNTs were functionalized with streptavidin by nonspecific adsorption [32-33]. Fluorescence microscopy of SWNTs with fluorescently labeled streptavidin indicated homogeneous coverage of the nanotubes with streptavidin [34].

Carbon nanotubes have several advantages for drug delivery: i) size in the range of 10-40 nm, ii) ability to provide a rod-like scaffold, iii) increased capacity to carry drugs, iv) ability to deliver drugs to the nucleus and v) inert and non-toxic nature. Researchers have obtained evidence showing the potential of carbon nanotubes in directed and targeted delivery of peptides and nucleic acids [35-36]. Moreover modification of nanotubes by adding certain functional groups enabled delivery of small peptides into the nuclei of fibroblast cells [37]. Although the mechanism of how tubes enter and leave cells is unclear, they appear to be non-toxic.

Chitosan has been shown to deliver genes into cells, but delivery of peptides by chitosan is limited. We reasoned that CNT coated with chitosan may facilitate peptide delivery and chitosan may reduce the toxicity of CNT to cells.

SUMMARY OF INVENTION

A functionalized single wall carbon nanotubes (SWCNT) complexed with nanochitosan for use in the delivery of bioaffecting substances and diagnostic applications.

In one aspect the present invention provides a functionalized carbon nanotube comprising a chitosan or a derivative thereof attached thereto wherein the chitosan species is operable to bind one or more biomolecules. In an advantageous embodiment the functionalized carbon nanotube further comprises one or more bioactive substances including peptides, proteins, nucleic acids and drugs.

In another aspect the present invention provides a method for preparing a chitosan single-walled carbon nanotubes comprising the steps of providing a functionalized carbon nanotube, providing a chitosan solution and contacting the functionalized carbon nanotube with the chitosan solution. The method can further include, within the step of providing a chitosan solution, the steps of dissolving chitosan or a derivative thereof in an about 0.05M HCl solution at a temperature of about 80° to about 90° to a concentration of about 0.5% by weight, reducing the temperature of the solution to room temperature and adjusting the pH of the solution to about 4.5 with concentrated potassium hydroxide. Additionally, the method can further include the step of complexing the chitosan single-walled carbon nanotubes with one or more nucleic acids or one or more peptides.

In still another aspect the present invention provides a method for delivering a desired biomolecule to a subject comprising the steps of providing a carbon nanotube chitosan complexed to a desired biomolecule and contacting a subject with the complexed carbon nanotube chitosan preparation. The desired biomolecule can be peptides, proteins, nucleic acids and drugs. The complexed carbon nanotube chitosan can delivered to effect drug delivery to the subject, effect diagnostics in the subject or it can be delivered as a biosensor for the subject.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1A:
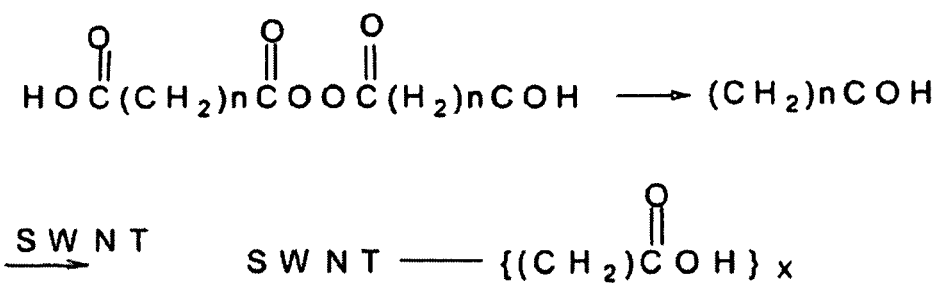
FIG. 1 is an illustration depicting the functionalization strategy for SWCNT.
Figure 1B:
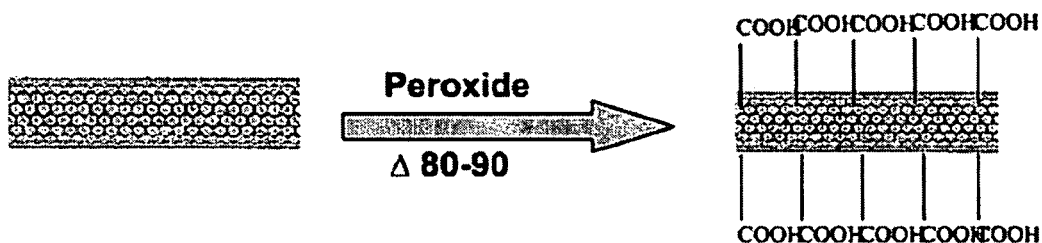

The disclosed invention is a system and method of drug delivery using carbon nanotube chitosan nanocomplexes. The organic functionalisation of carbon nanotubes can improve substantially their solubility and biocompatibility profile; as a consequence, their manipulation and integration into biological systems has become possible so that functionalised carbon nanotubes hold currently strong promise as novel systems for the delivery of drugs, antigens and genes. [Biomedical applications of functionalised carbon nanotubes. *Chem Commun (Camb)*. Feb. 7, 2005; (5):571-7. Epub Dec. 21, 2004] Additionally, in the medical diagnostics arena, nanotechnology-based biosensors could be used to replace more costly and tedious laboratory methods for monitoring a patient's blood for proteins, chemicals, and pathogens.

The term "chitosan", as used herein, will be understood by those skilled in the art to include all derivatives of chitin, or poly-N-aceryl-D-glucosamine (including all polyglucosamine and oligomers of glucosamine materials of different molecular weights), in which the greater proportion of the N-acetyl groups have been removed through hydrolysis. Generally, chitosans are a family of cationic, binary heteropolysaccharides composed of (1→4)-linked 2-acetamido-2-deoxy-β-D-glucose (GlcNAc, A-unit) and 2-amino-2-deoxy-β-D-glucose, (GlcN; D-unit) (Varum K. M. et al., *Carbohydr. Res.*, 1991, 217:19-27; Sannan T. et al., *Macromol. Chem.*, 1776, 177:3589-3600). Preferably, the chitosan has a positive charge. Chitosan, chitosan derivatives or salts (e.g., nitrate, phosphate, sulphate, hydrochloride, glutamate, lactate or acetate salts) of chitosan may be used and are included within the meaning of the term "chitosan". As used herein, the term "chitosan derivatives" are intended to include ester, ether or other derivatives formed by bonding of acyl and/or alkyl groups with OH groups, but not the $NH_2$ groups, of chitosan. Examples are O-alkyl ethers of chitosan and O-acyl esters of chitosan. Modified chitosans, particularly those conjugated to polyethylene glycol, are included in this definition. Low and medium viscosity chitosans (for example CL113, G210 and CL10) may be obtained from various sources, including PRONOVA Biopolymer, Ltd. (UK); SEIGAGAKU America Inc. (Maryland, USA); MERON (India) Pvt, Ltd. (India); VANSON Ltd. (Virginia, USA); and AMS Biotechnology Ltd. (UK). Suitable derivatives include those which are disclosed in Roberts, Chitin Chemistry, MacMillan Press Ltd., London (1992). Optimization of structural variables such as the charge density and molecular weight of the chitosan for efficiency of polynucleotide delivery and expression is contemplated and encompassed by the present invention.

Functionalized Single Wall Carbon Nanotube (SWCNT) complexed with nanochitosan NG042 were used for delivery of DNA encoding EGFP reporter protein and peptide. A scanning electron micrograph of a cluster of functionalized SWCNT and acid-functionalized and coated with NG042 protein were performed to understand the binding of the peptide and DNA with SWCNT. Groups of mice were administered with SWNT particles to determine the efficiency of transfection. After 24 h their lungs were lavaged and BAL cells were examined under fluorescent microscope after staining with DAPI. BAL cells from mice given NG042-TR without CNT were used as control (−). The results demonstrate that shown CNT-chitosan hybrid nanoparticles exhibit significantly higher transfection efficiency in vivo than chitosan alone. Furthermore, the functionalized nanotubes were tested for peptide transfer into HEK293 cells. The results showed that the hybrid nanoparticles efficiently transferred peptides. Together, these results show that hybrid SWCNT-chitosan particles increase DNA and peptide transfer into cells.

The invention will be further described by way of the following non-limiting examples.

Example 1

Preparation of Functionalized Single Walled Carbon Nanotubes (fSWCNT)

Step 1. To prepare peroxide (succinic) 10 g of succinic anhydride fine powder was added to 20 mL of ice cold 8% hydrogen peroxide and stirred for 30 min until all of the powder dissolved and a white gel like solution formed. The solution was filtered onto a 1-micrometer pore size PTFE membrane (Cole Palmer) to leave a deposit which was washed with a small amount of water and air-dried for 10 min. The white peroxide products were transferred from the membrane to a glass vial and vacuum-dried at room temperature for 24 h. The succinic peroxide yield was obtained about 5.8 g using this one-step procedure [38].

Step 2. Preparation of acid-functionalized SWCNTs. Purified SWCNTs (50 mg) were placed in a 250-mL flask filled with 50 mL of dry o-dichlorobenzene and sonicated with 2510 Braison bath for 30 min to obtain a SWCNT suspension solution. The SWCNT suspension, heated with 1 gram of peroxide at 80-90° C. for 10 days (synthesized in step 1) (FIG. 1a) After the reaction was complete, the suspension was cooled and poured into a 500-mL flask containing a large amount of tetrahydrofuran and sonicated for 15 min. The obtained solution was filtered using a 0.2-micrometer pore size PTFE membrane (Cole Palmer). Functionalized SWCNTs were collected on the membrane, then placed in 100 mL of ethanol, sonicated for 20 min, and then filtered again. During the filtration, a large amount of ethanol was repeatedly used to completely wash off the unreacted peroxides and the reaction byproducts. Finally, the functionalized SWCNTs were vacuum-dried at 70° C. overnight. SWCNT (Sigma) was acid functionalized as per the reaction shown below.

Example 2

Preparation of f-CNT Chitosan DNA Complexes

Figure 2:
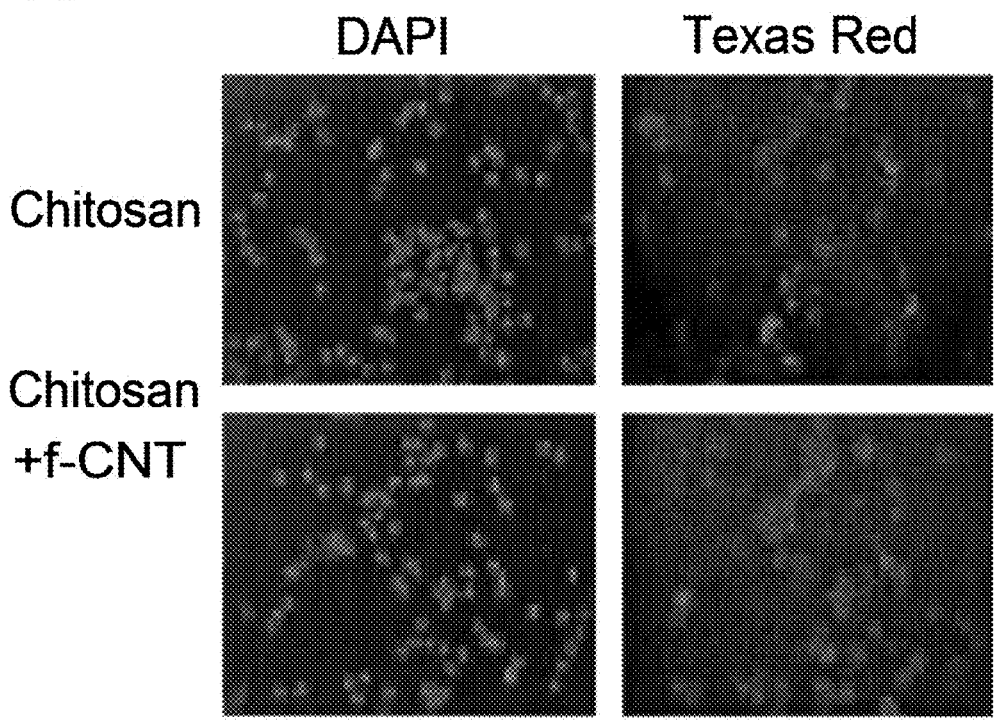
FIG. 2 illustrates the transduction of efficiency of f-SWCNT-chitosan for delivery of peptide. (A) Fluorescent microscopy of chitosan transduced BAL cells. (B) Percent chitosan positive cells quantified from A.
Figure 2:
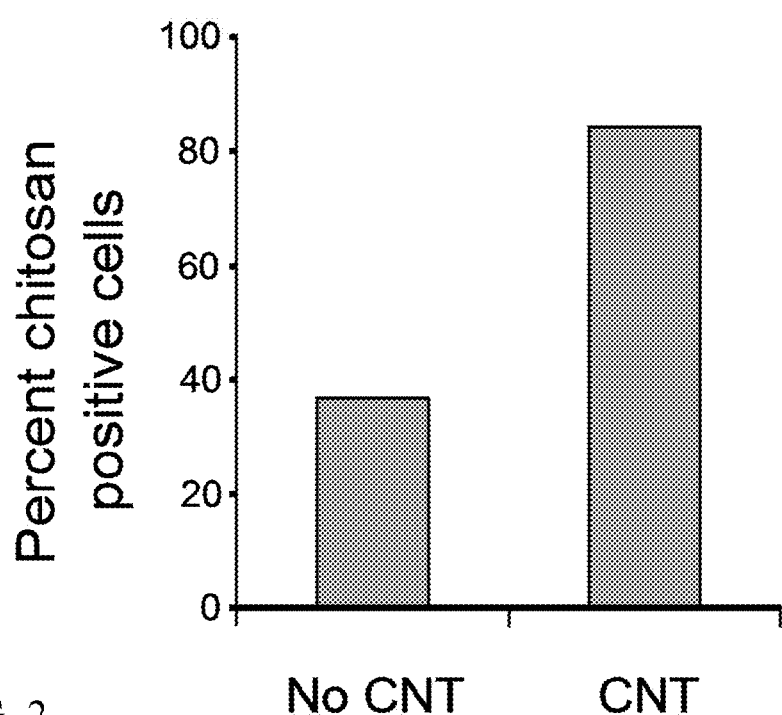

SWNTs were then complexed with nanochitosan NG042 and further complexed with DNA encoding EGFP reporter protein. SWCNTs were characterized by scanning electron micrograph of a cluster of functionalized SWCNT (left) and acid-functionalized and coated with NG042 (FIG. 2).

Step 1—Solutions of Chitosan and Carbon Nanotubes

Chitosan is soluble in acidic aqueous solutions in which it behaves as a cationic polyelectrolyte. At pH 6 chitosan flocculated due to the deprotonation of its amine groups. A 0.50 wt % chitosan stock solution was prepared by dissolving chitosan flakes in hot 0.05 M HCl solution (80-90° C.). The solution was cooled to room temperature, and its pH was adjusted to 4.5 using a concentrated KOH solution. The chitosan solution was filter and stored in a refrigerator (4° C.). The carbon nanatubes were solubilized in chitosan solutions (0.50-5 rug of CNT $mL^{-1}$) using a short 15-ruin sonication and then vigorously stirred for 6 kits at 40° C. [39].

Step 2—Preparation of Carbon Nanotube-Chitosan-DNA Complexes

The appropriate volume of nanotube coupled with chitosan was diluted in 500 microliters of DI water and stored in 100 microliter aliquots. The CNT concentrations in this stock solution was about 50 microgram/mL. Then plasmid DNA was mixed with CNT-coupled chitosan solution in a ratio of 1:5 (w/w), and stirred for 12 hrs. The f-CNTchitosan-DNA complex was washed with 50 microliter DI water and centrifugation. Then the complexes were allowed to settle for 30 min at room temperature prior to use.

Example 3

Preparation of Peptide-f-SWNT Samples

SWNTs were obtained from Sigma USA. A FITC labeled ANP peptide solutions was prepared by dissolving 3 mg of peptide in 300 microliter DI water and peptide concentrations were verified using UV-Vis absorption spectrometry. The 50 microgram of f-SWNTs were dispersed in 1 mL DI water. The 1:5 ratio mixtures of peptide and f-SWCNT were vortexed for approximately 60 min and left over night at 4° C. Next day sonication was performed using a Branson Sonifier 2150 with the sample immersed in an ice water bath for 25 min., yielding dense black mixtures. The sonicated samples were first centrifuged in an Eppendorf 5415D centrifuge for 5 min. The upper 75% of the supernatant was recovered using a small-bore piped, avoiding sediment at the bottom, and transferred to a centrifuge tube for further centrifugation. Samples were then centrifuged for 30 min. The upper 50% of the supernatant was recovered using a small-bore piped, avoiding sediment at the bottom, and transferred to a clean tube. Centrifugation of SWNTs-peptide complex formed insoluble pellet. The pellet was dissolved in DI water and used for experiments.

Example 4

Transfection Assay

The potential of f-SWCNT-chitosan-DNA complex was tested in vivo using mice. Groups of mice were administered with f-SWNT particles to determine the efficiency of transfection. Then SWCNT was surface coated with Texas red-labeled NG042 (NG042-TR) and given intranasally to groups of mice (n=3). After 24 hr, their lungs were lavaged and BAL cells were examined under fluorescent microscope after staining with DAPL BAL cells from mice given NG042-TR without CNT were used as control (−). For peptide delivery, HEK293 cells were transduced with FITC-labeled NP73-102 peptide using functionalized SWCNT. The cells were transduced using 8 well chamber plates with 1 microgram of peptide per well. After 24 h, cells were examined under fluorescent microscope after staining with DAPI. Cells given peptide without CNT were used as control (−).

Example 5

Characterization of SWCNT with and without Functionalization

Figure 4:
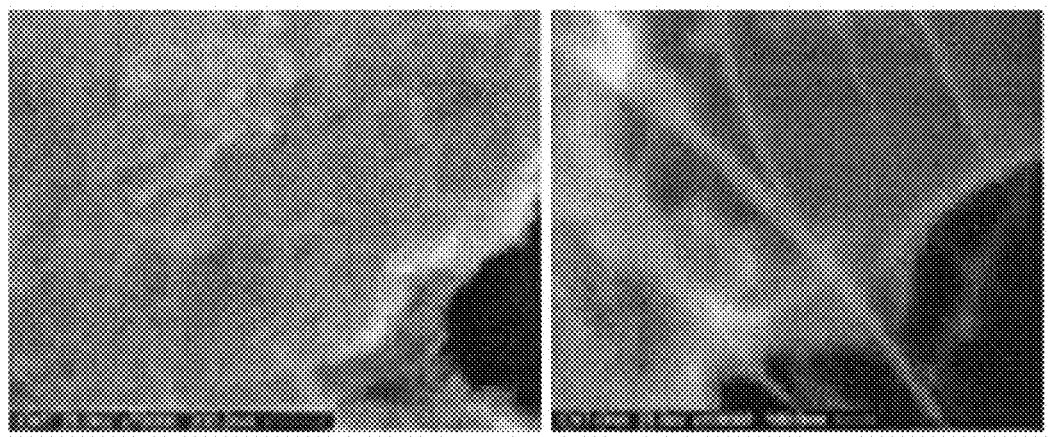
FIG. 4 is a scanning electron micrograph (SEM) of functionalized carbon nanotubes.

Surface functionalization enables adsorption or attachment of various molecules or antigens, which subsequently can be targeted to the desired cell population for immune recognition or a therapeutic effect. SEM (Hitachi S-800) was employed to characterize the morphologies of the SWCNT with and without functionalization as shown in FIG. 4. Carbon nanotubes (f-SWCNTs) in SEM are observed as bundles of different diameter and length without functionalization. After functionalization, SWCNTs are visualized as single entities which indicated the formation of nanotube-DNA complexes. The f-SWCNTs were presented in bundles of different diameters on which the plasmid DNA was condensed by forming super coiled structures. This observation was extremely encouraging for the subsequent planning of gene delivery and expression experiments.

Example 6

Functionalized SWCNT as a Gene Carrier System

With the aim of developing different alternative gene carrier systems, we examined the potential of functionalized and chitosan-coated SWCNTS. We reasoned that the hybrid particles of SWCNT and chitosan may enhance chitosan delivery into cells. Functionalization of their surface can result in uniform suspensions, which can be further derivatized with active molecules, making them compatible with biological systems. This idea was tested using Texas red-labeled chitosan in mice. In vivo transduction of SWCNT was surface coated with Texas red-labeled NG042 (NG042-TR) and given intranasally to groups of mice (n=3) and 24 hr after their lungs were lavaged and BAL cells were examined under fluorescent microscope after staining with DAPI. BAL cells from mice given NG042-TR without CNT were used as control (−). To determine whether CNT facilitated chitosan incorporation into cells, BAL cells were observed under fluorescent microscope (FIG. 2A). The cells were counted for DAPI (nuclear) and Red staining and % chitosan positive cells was determined (FIG. 2B) The results demonstrate that f-SWCNT chitosan is more effective in chitosan uptake into cells.

Example 7

Functionalized SWCNT as a Peptide Delivery System

Figure 3:
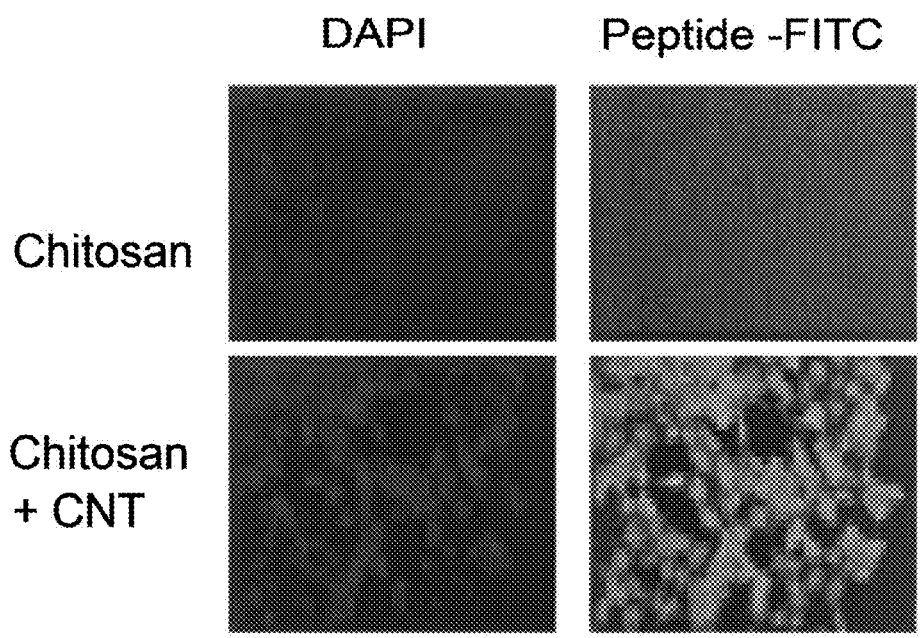
FIG. 3 is a series of photographs demonstrating that CNT enabled chitosan to deliver peptides into cells.

For peptide delivery, HEK293 cells were transduced with FITC-labeled NP73-102 peptide using functionalized SWCNT. The cells were transduced in well 8-chamber plates with 1 microgram of peptide. After 24 h cells were examined under fluorescent microscope after staining with DAPI. Cells given peptide without CNT were used as control (−). Results show that f-SWCNT-chitosan significantly increases peptide delivery to the cells (FIG. 3)

These results together demonstrates that surface functionalization of SWCNT and coated with chitosan, NG042, enables adsorption or attachment of various molecules including peptides, which subsequently can be targeted to the desired cell population for immune recognition or a therapeutic effect. Functionalized nanotubes may act as building blocks for the preparation of nylon-type cross-linked single-walled carbon nanotube-polymers. These tubes can also covalently bind to DNA and drugs and, if made soluble, might serve as nanovehicles for drug delivery. In this report, we tested the possibility of combining CNTs with polymeric chitosan to improve their potential to deliver nucleic acids and peptides. It may broaden the application of carbon nanotube technology for diverse biomedical applications, including diagnostics, biosensor development and pharmaceutics.

Example 8

Further Applications of Functionalized Chitosan SWCNT Systems

Carbon nanotubes are man-made one-dimensional carbon crystals with different diameters and chiralities. Owing to their superb mechanical and electrical properties, many potential applications have been proposed for them. However, polydispersity and poor solubility in both aqueous and non-aqueous solution impose a considerable challenge for their separation and assembly, which is required for many applications. Here researchers have reported DNA-assisted dispersion and separation of carbon nanotubes. Bundled single-walled carbon nanotubes are effectively dispersed in water by their sonication in the presence of single-stranded DNA (ssDNA). Optical absorption and fluorescence spectroscopy and atomic force microscopy measurements provide evidence for individually dispersed carbon nanotubes. Molecular modelling suggests that ssDNA can bind to carbon nanotubes through pi-stacking, resulting in helical wrapping to the surface. The binding free energy of ssDNA to carbon nanotubes rivals that of two nanotubes for each other. DNA-coated carbon nanotubes can be separated into fractions with different electronic structures by ion-exchange chromatography. This finding links one of the central molecules in biology to a technologically very important nanomaterial, and opens the door to carbon-nanotube-based applications in biotechnology. [DNA-assisted dispersion and separation of carbon nanotubes *Nat Mater*. May 2, 2003(5):338-42]

Wrapping of carbon nanotubes (CNTs) by single-stranded DNA (ssDNA) was found to be sequence-dependent. A systematic search of the ssDNA library selected a sequence d(GT)n, n=10 to 45 that self-assembles into a helical structure around individual nanotubes in such a way that the electrostatics of the DNA-CNT hybrid depends on tube diameter and electronic properties, enabling nanotube separation by anion exchange chromatography. Optical absorption and Raman spectroscopy show that early fractions are enriched in the smaller diameter and metallic tubes, whereas late fractions are enriched in the larger diameter and semiconducting tubes. [Structure-based carbon nanotube sorting by sequence-dependent DNA assembly. *Science*. Nov. 28, 2003; 302(5650): 1545-8.]

Because of their nanometer sizes and molecular recognition capabilities, biological systems have garnered much attention as vehicles for the directed assembly of nanoscale materials. One of the greatest challenges has been to successfully interface biological systems with electronic materials, such as semiconductors and metals. As a means to address some of these issues, through a systematic analysis, it was found that short oligonucleotides having repeating sequences of gunanines and thymines (dGdT)(n) could wrap in a helical manner around a CNT with periodic pitch. Although helix formation around SWCNTs having regular pitches is an effective method for dispersing and separating CNTs, the need for specific repeating sequences limits use to non-natural DNA that must be synthesized with optimal lengths of less than 150 bases. In contrast, long genomic single-stranded DNA (>>100 bases) of a completely random sequence of bases can be used to disperse CNTs efficiently through the single-stranded DNA's (ssDNA) ability to form tight helices around the CNTs with distinct periodic pitches, although this process occurs irrespective of the DNA sequence. [Sequence-independent helical wrapping of single-walled carbon nanotubes by long genomic DNA. *Nano Lett*. Feb. 6, 2003; (2): 159-64.]

Carbon nanotubes (CNTs) constitute a class of nanomaterials that possess characteristics suitable for a variety of possible applications. Their compatibility with aqueous environments has been made possible by the chemical functionalization of their surface, allowing for exploration of their interactions with biological components including mammalian cells. Functionalized CNTs (f-CNTs) are being intensively explored in advanced biotechnological applications ranging from molecular biosensors to cellular growth substrates. f-CNTs offer great potential as delivery vehicles of biologically active molecules in view of possible biomedical applications, including vaccination and gene delivery. The capability of ammonium-functionalized single-walled CNTs to penetrate human and murine cells and facilitate the delivery of plasmid DNA leading to expression of marker genes has been shown. To optimize f-CNTs as gene delivery vehicles, it is essential to characterize their interactions with DNA. The interactions of three types of f-CNTs, ammonium-functionalized single-walled and multiwalled carbon nanotubes (SWNT-$NH_3+$; MWNT-$NH_3+$), and lysine-functionalized single-walled carbon nanotubes (SWNT-Lys-$NH_3+$), with plasmid DNA have been compared. The results indicate that all three types of cationic carbon nanotubes are able to condense DNA to varying degrees, indicating that both nanotube surface area and charge density are critical parameters that determine the interaction and electrostatic complex formation between f-CNTs with DNA. All three different f-CNT types in this study exhibited upregulation of marker gene expression over naked DNA using a mammalian (human) cell line. Differences in the levels of gene expression were correlated with the structural and biophysical data obtained for the f-CNT:DNA complexes to suggest that large surface area leading to very efficient DNA condensation is not necessary for effective gene transfer. However, it will require further investigation to determine whether the degree of binding and tight association between DNA and nanotubes is a desirable trait to increase gene expression efficiency in vitro or in vivo. [Binding and condensation of plasmid DNA onto functionalized carbon nanotubes: toward the construction of nanotube-based gene delivery vectors. *J Am Chem Soc*. Mar. 30, 2005; 127(12):4388-96]

Functionalised carbon nanotubes (f-CNTs) are emerging as new tools in the field of nanobiotechnology and nanomedicine. This is because they can be easily manipulated and modified by encapsulation with biopolymers or by covalent linking of solubilising groups to the external walls and tips. The possibility of incorporating f-CNTs into biological systems has opened the way to the exploration of their potential applications in biology and medicinal chemistry. Within the different fields of applications (i.e., biosensors, composite materials, molecular electronics), one use of CNTs is as new carrier systems for the delivery of therapeutic molecules. [Carbon nanotubes for the delivery of therapeutic molecules. *Expert Opin Drug Deliv.* Nov. 1, 2004 (1):57-65.]

The development of new and efficient drug delivery systems is of fundamental importance to improve the pharmacological profiles of many classes of therapeutic molecules. Many different types of drug delivery systems are currently available. Within the family of nanomaterials, carbon nanotubes (CNT) have emerged as a new alternative and efficient tool for transporting and translocating therapeutic molecules. CNT can be functionalised with bioactive peptides, proteins, nucleic acids and drugs, and used to deliver their cargos to cells and organs. Because functionalised CNT display low toxicity and are not immunogenic, such systems hold great potential in the field of nanobiotechnology and nanomedicine. [Applications of carbon nanotubes in drug delivery. *Curr Opin Chem Biol.* Dec. 9, 2005 (6):674-9. Epub Oct. 17, 2005]

Carbon nanotubes are considered as molecular wires exhibiting novel properties for diverse applications including medicinal and biotechnological purposes. Surface chemistry on carbon nanotubes results on their solubilization in organic solvents and/or aqueous/physiological media. Herein, we will present how interfacing such novel carbon-based nanomaterials with biological systems may lead to new applications in diagnostics, vaccine and drug delivery. Recent developments in this rapidly growing field will be presented thus suggesting exciting opportunities for the utilization of carbon nanotubes as useful tools for biotechnological applications. Emphasis will be placed in the integration of biomaterials with carbon nanotubes, which enables the use of such hybrid systems as biosensor devices, immunosensors and DNA-sensors. [Carbon nanotubes: materials for medicinal chemistry and biotechnological applications *Curr Med Chem.* 2006; 13(15):1789-98].

Carbon nanotubes (CNTs) revealing metallic or semiconductive properties depending on the folding modes of the nanotube walls represent a novel class of nanowires. Different methods to separate semiconductive CNTs from conductive CNTs have been developed, and synthetic strategies to chemically modify the side walls or tube ends by molecular or biomolecular components have been reported. Tailoring hybrid systems consisting of CNTs and biomolecules (proteins and DNA) has rapidly expanded and attracted substantial research effort. The integration of biomaterials with CNTs enables the use of the hybrid systems as active field-effect transistors or biosensor devices (enzyme electrodes, immunosensors, or DNA sensors). Also, the integration of CNTs with biomolecules has allowed the generation of complex nanostructures and nanocircuitry of controlled properties and functions. [Biomolecule-functionalized carbon nanotubes: applications in nanobioelectronics *Chemphyschem.* Aug. 20, 2004; 5(8): 1084-104]

REFERENCES

Kong, J.; Franklin, N. R.; Thou, C.; Chapline, M. G.; Peng, S.; Cho, K.; Dai, H. *Science* 2000, 287, 622.

Li., Z.; Chen, V; Li, X.; Kamins, T. 1.; Nanka, K.; Williams, R. S. *Nano Lett.* 2004, 4, 245.

Hahm, 1; Lieber, C, *Nano Left.* 2004, 4, 51.

Zheng, M.; Jagota, A.; Strano, M. S.; Santos, A. P.; Barone, P.; Chou, S. C L; Diner, B. A.; Dresselhaus M. S.; McLean, P. S.; Onoa, G. B.; Sanisonidze, O. O; Semke, B. D.; Usrey, M. L; Walls, D. J. *Science* 2003, 302, 1545-48.

Zheng, M.; Jagota, A.; Semke, B. D.; Diner, B. A.; McLean, P. S.; Lustig, S. R.; Richardson, R. B.; Tassi, N. G. *Nat. Mater.* 2003, 2, 338-342.

Strano, M. S.; Zheng, M.; Jagota, A.; Onoa, O. B.; Heilcr, 1), A.; Rarone, P. W.; Usrey, M. L. *Nano Left,* 2004, 4, 543-50.

Niemeyer, C. M., Mirkin, C. A., Eds. *Nanobiotechnology: Concepts, Applications and Perspectives*; Wiley-VCH: Weinheim, Germany, 2004.

Moghimi, S. M; Hunter, A. C.; Murray, 3. C. *Pharmacol. ReV.* 2001, 53, 283-318.

Zhang, S. *Nat. Biotechnol.* 2003, 21, 1171-1178.

Wong, S. S.; Joselevich, B.; Woolley, A. T.; Cheung, C. L.; Lieber, C. M. *Nature* 1998, 394, 52-55.

Hirsch, A. *Angew. Chem, In:* Er. 2002, 41, 1853-1859. (b) Dyke, C. A.; Tour, 3. M. *Chetn. Eur. J.* 2004, 10, 813-817.

Zheng, M.; Jagota, A.; Semke, B. D.; Diner, B. A.; McLean, R. S.; Lustig, S. R.; Richardson, R. B.; Tassi, N. O. *Nat. Mater.* 2003, 2, 338-342.

Hui, H.; Yingchun, N.; Vedrana, M.; Haddon, R. C.; Parpura, V. *Náno Let:* 2004, 4, 507-511. (b) Mattson., M. P.; Hadclon, R. C.; Rao, A. M. *J. Mol. Neurosci.* 2000, 14, 175-182.

Mitchell, D, T.; Lee, S. B.; Trofin, L.; Li, N.; Nevanen, T. K.; Soderhmd, H.; Martin, C. R. *J. Am. Chem. Soc.* 2002, 124, 11864-11865.

Keren. K.; Berman, R.; Buchstab, B.; S:ivan, U.; Braun, B. *Science* 2003, 302, 1380.

Hazani, M L; Hennrich, F.; Kappes, M.; Naaman, R.; Peled, D.; Sidorov, V.; Shvarts, 1). *Chem. Phys. Left.* 2004, 391, 389.

Li, J.; Ng, H. T.; Cassefl, A.; Fan, W.; Chen, H.; Ye, Q.; Kochne, 3.; Han, 3; Mey) ppan, ML *Nano Left.* 2003, 3, 597.

Moghakiam, M.; Taylor, S.; Gao, M.; Huang, S.; Dai, L; McCall, M. 3. *Nano Left.* 2004, 4, 89.

Gao, H., Kong Y., Ciii, I)., Ozkan, C. S., 2003. Spontaneous insertion of DNA oiigonucleottdes into carbon nanotubes. Nano. Lett. 3, 471-473.

Cui, D., Gao, H., 2003. Advance and prospect of bionanomaterials. Biotechnol. Prog. 19, 683-692.

Cui, D., Ozkan, C S., Ravindran, S., KonY., Gao, H., 2004, Mach. Chem. Biosystems 1, 113-121.

Shini, M L, Karn, N. W. S., Chen, R I., Li, Y., Dal, H., 2002, Nano Lett. 2, 285-288.

Bahr J. L., Tour, J. M., 2002, J. Mater. Chem. 12, 1952-1958.

Robert, F., 2003, Science 300,243.

Mattson, M. P., Haddot. R C., Rao, A. M., 2001, J. Mol. Neurosci. 14, 175-182.

Chan, H. C., Kuo, S. C., Huang, Li., Liu, C H., Han, S. L, 2003, Eur. 3. Pharma. 467, 31-39.

Maynani, A. D., Baron, P A, Foley, M., Sbvedova, A. A., I jam, E. R., Castranova, V., 2004.3. Toxicol. Environ. Health A 67, 87-107.

Lam, C. W., James, J. T., McCluSkey, I L, Hunter, iLL., 2004. Toxicol. Sd. 7?, 126-134.

Maragakis, P.; Barnett, R. L.; Kaxiras, E.; Bistner, M L; Frauenheim, lix. *Phys. ReV. B* 2002, 66, 241104.

Macke, T.; Case: D. In *Modeling unusal nucleic acid structures*; Leontes, N., Santa Lucia, J., Ed.; American Chetnical Society Washington, D.C., 1.998; pp 379-393.

Brooks, B. Ct al. *J. Canqnst. Chem.* 1983, 4, 187.

F. Balavoine et al. *Angew. Chem. mt. Ed.* 38 1912 (1999).

M. Shim, N. W. S. Kani, I L 3. Chcn, Y. Li, H. Dai, *Nano Letters* 2(4)128:5 (2002). 1:2

J. Liu et al., *Science* 280, 1253 (1998),

K. A. Williams, P. T. M. Veenbuizen, B. Cl. de Ia Torre, R. Eritjia and C. Dekker, Nature, 2002, 420, 761.

C. V. Nguyen, L. Deizeit, A. M. Cassel, 3. Li, 3. Han and M. Meyyappan, Nano Lett., 2002, 2, 1079.

Alberto Bianco, Kostas Kostarelos, Charalambos D. Partidos and Maurizio Prato Chem. Commun., 2005, 571-577.

Clover. A. M.; Houghton, A. C. *Am. Chem. J.* 1904, 32, 55.

Maogen Zhang. Audrey Smith, and Waldemar Gorsk, Anal. Chem. 2004, 76, 5015.5050.

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for preparing a compound comprising the steps of:
    providing a functionalized carbon nanotube, wherein the functionalized nanotube further comprises:
        a single walled carbon nanotube structure;
        at least one functional group directly bonded to at least one carbon in the carbon nanotube structure, wherein the function group is $[(CH_2)CO_2H]_x$, COOH, ammonium, or lysine;
    providing a chitosan solution;
    contacting the functionalized carbon nanotube with the chitosan solution to form a chitosan coating;
    providing at least one biomolecule; and
    complexing the at least one biomolecule to the chitosan coating.

2. The method of claim 1 wherein the step of providing the chitosan solution includes the steps of:
    dissolving chitosan or a derivative thereof in an about 0.05M hydrochloric acid solution at a temperature of about 80° to about 90° to a concentration of about 0.5% by weight;
    reducing the temperature of the solution to room temperature; and
    adjusting the pH of the solution to about 4.5 with concentrated potassium hydroxide.

3. The method according to claim 1 wherein the at least one biomolecule is one or more nucleic acids, one or more peptides, or drugs.

4. The method of claim 1 wherein the step of providing a functionalized carbon nanotube further comprises the steps
    functionalizing the carbon nanotube structure, comprising the steps
        suspending the carbon nanotube structure in o-dichlorobenzene to form a suspension;
        heating the suspension to 80-90° C. for 10 days;
        cooling the suspension; and
        filtering the cooled suspension.

5. The method of claim 1 wherein the biomolecule is complexed in a solution having a ratio of 1:5 ratio of biomolecule to chitosan coated-functionalized carbon nanotube.

6. The method of claim 1 wherein the functionalized carbon nanotube is ammonium-functionalized single-walled carbon nanotubes, or lysine-functionalized single-walled carbon nanotubes.

7. A method for delivering a desired biomolecule to a subject comprising the steps of:
    providing a carbon nanotube chitosan complexed to a desired biomolecule wherein the carbon nanotube chitosan further comprises:
        a functionalized carbon nanotube, wherein the functionalized nanotube further comprises:
            a carbon nanotube structure;
            at least one functional group bonded to at least one carbon in the carbon nanotube structure, wherein the function group is $[(CH_2)CO_2H]_x$, COOH, ammonium, or lysine;
        a chitosan coating complexed to the carbon nanotube structure; and
        at least one biomolecule complexed to the chitosan coating; and
    contacting a subject with the complexed carbon nanotube chitosan preparation.

8. The method according to claim 7 wherein the desired biomolecule is selected from the group consisting of peptides, proteins, nucleic acids and drugs.

9. The method according to claim 7 wherein the complexed carbon nanotube chitosan is delivered to effect drug delivery to the subject.

10. The method according to claim 7 wherein the complexed carbon nanotube chitosan is delivered to effect diagnostics in the subject.

11. The method according to claim 7 wherein the complexed carbon nanotube chitosan is delivered as a biosensor for the subject.

12. A compound comprising:
    a functionalized carbon nanotube, wherein the functionalized nanotube further comprises:
        a carbon nanotube structure, wherein the carbon nanotube structure is single wall carbon nanotube;
        at least one functional group bonded to at least one carbon in the carbon nanotube structure, wherein the function group is $[(CH_2)CO_2H]_x$, COOH, ammonium, or lysine;
    a chitosan coating complexed to the carbon nanotube; and
    at least one biomolecule complexed to the chitosan coating.

13. The compound according to claim 12, wherein the at least one biomolecule is selected from the group consisting of peptides, proteins, nucleic acids and drugs.

14. The compound of claim 12 wherein the functionalized carbon nanotube is ammonium-functionalized single-walled carbon nanotubes, or lysine-functionalized single-walled carbon nanotubes.

15. A composition comprising:
    at least one functionalized carbon nanotube, wherein the functionalized nanotube further comprises:
        a carbon nanotube structure;
        at least one functional group bonded to at least one carbon in the carbon nanotube structure, wherein the function group is $[(CH_2)CO_2H]_x$, COOH, ammonium, or lysine;
    a chitosan coating complexed to the carbon nanotube structure; and
    at least one biomolecule complexed to the chitosan coating to form a drug delivery molecule;
    wherein the drug delivery molecule is suspended in solution.

16. The functionalized carbon nanotube according to claim 15, wherein the at least one biomolecule is selected from the group consisting of peptides, proteins, nucleic acids and drugs.

17. The compound according to claim 15 wherein the carbon nanotube structure is single wall carbon nanotube.

18. The composition of claim 15 wherein the functionalized carbon nanotube is ammonium-functionalized single-walled carbon nanotubes, ammonium-functionalized multi-walled carbon nanotubes, or lysine-functionalized single-walled carbon nanotubes.

* * * * *

UNITED STATES PATENT AND TRADEMARK OFFICE
CERTIFICATE OF CORRECTION

| | | |
|---|---|---|
| PATENT NO. | : 8,536,324 B2 | Page 1 of 1 |
| APPLICATION NO. | : 12/105884 | |
| DATED | : September 17, 2013 | |
| INVENTOR(S) | : Shyam S. Mohapatra and Arun Kumar | |

It is certified that error appears in the above-identified patent and that said Letters Patent is hereby corrected as shown below:

In the Specification, please add the following paragraph:

STATEMENT OF GOVERNMENT INTEREST

This invention was made with government support under Grant # R01 HL071101 awarded by National Institutes of Health. The government has certain rights in the invention.

Signed and Sealed this
Sixteenth Day of June, 2015

Michelle K. Lee
*Director of the United States Patent and Trademark Office*